(12) United States Patent
Manassen et al.

(10) Patent No.: US 9,921,050 B2
(45) Date of Patent: Mar. 20, 2018

(54) SPECTRAL CONTROL SYSTEM

(71) Applicant: KLA-Tencor Corporation, Milpitas, CA (US)

(72) Inventors: Amnon Manassen, Haifa (IL); Andrew V. Hill, Sunnyvale, CA (US); Ohad Bachar, Timrat (IL); Avi Abramov, Haifa (IL); Daria Negri, Nesher (IL)

(73) Assignee: KLA—Tencor Corporation, Milpitas, CA (US)

( * ) Notice: Subject to any disclaimer, the term of this patent is extended or adjusted under 35 U.S.C. 154(b) by 0 days.

(21) Appl. No.: 15/098,008

(22) Filed: Apr. 13, 2016

(65) Prior Publication Data
US 2016/0305766 A1 Oct. 20, 2016

Related U.S. Application Data

(62) Division of application No. 13/945,352, filed on Jul. 18, 2013, now Pat. No. 9,341,769.
(Continued)

(51) Int. Cl.
*G02B 27/10* (2006.01)
*G01B 11/02* (2006.01)
(Continued)

(52) U.S. Cl.
CPC .............. *G01B 11/02* (2013.01); *F21V 5/02* (2013.01); *F21V 5/04* (2013.01); *F21V 9/10* (2013.01); *F21V 14/08* (2013.01); *G01N 21/55* (2013.01); *G02B 5/18* (2013.01); *G02B 5/205* (2013.01); *G02B 6/0005* (2013.01); *G02B 6/02* (2013.01); *G02B 26/008* (2013.01); *G02B 26/023* (2013.01); *G02B 26/04* (2013.01); *G02B 26/0816* (2013.01); *G02B 27/1026* (2013.01); *G02B 27/141* (2013.01); *G02B 27/146* (2013.01); *G02B 6/3512* (2013.01); *G02B 6/4215* (2013.01)

(58) Field of Classification Search
CPC .... G02B 27/10; G02B 27/144; G02B 27/145; G02B 27/146; H04Q 1/005; H04Q 2011/0015; H04Q 2011/009; H04Q 2011/0026
USPC ..................................... 359/618; 385/16, 17
See application file for complete search history.

(56) References Cited

U.S. PATENT DOCUMENTS

| | | |
|---|---|---|
| 2003/0161039 A1 | 8/2003 | Fukano et al. |
| 2005/0073742 A1 | 4/2005 | Weyh et al. |

(Continued)

FOREIGN PATENT DOCUMENTS

JP 2011191199 A 9/2011

*Primary Examiner* — William Choi
(74) *Attorney, Agent, or Firm* — Suiter Swantz PC LLO

(57) ABSTRACT

The disclosure is directed to a system and method of controlling spectral attributes of illumination. According to various embodiments, a portion of illumination including an excluded selection of illumination spectra is blocked, while another portion of the illumination including a transmitted selection of illumination spectra is directed along an illumination path. In some embodiments, optical metrology is performed utilizing the spectrally controlled illumination to enhance measurement capability. For instance, the spectral attributes of illumination utilized to analyze different portions of a sample, such as different semiconductor layers, may be selected according to certain measurement characteristics associated with the analyzed portions of the sample.

28 Claims, 10 Drawing Sheets

Related U.S. Application Data

(60) Provisional application No. 61/738,322, filed on Dec. 17, 2012, provisional application No. 61/808,555, filed on Apr. 4, 2013.

(51) Int. Cl.

| | |
|---|---|
| *G01N 21/55* | (2014.01) |
| *G02B 6/02* | (2006.01) |
| *G02B 26/00* | (2006.01) |
| *G02B 27/14* | (2006.01) |
| *G02B 26/02* | (2006.01) |
| *F21V 5/02* | (2006.01) |
| *F21V 5/04* | (2006.01) |
| *F21V 9/10* | (2006.01) |
| *F21V 14/08* | (2006.01) |
| *G02B 5/18* | (2006.01) |
| *G02B 5/20* | (2006.01) |
| *F21V 8/00* | (2006.01) |
| *G02B 26/04* | (2006.01) |
| *G02B 26/08* | (2006.01) |
| *G02B 6/35* | (2006.01) |
| *G02B 6/42* | (2006.01) |

(56) References Cited

U.S. PATENT DOCUMENTS

| | | |
|---|---|---|
| 2007/0273798 A1 | 11/2007 | Silverstein et al. |
| 2007/0279636 A1 | 12/2007 | Li et al. |
| 2010/0314554 A1 | 12/2010 | Galimberti et al. |

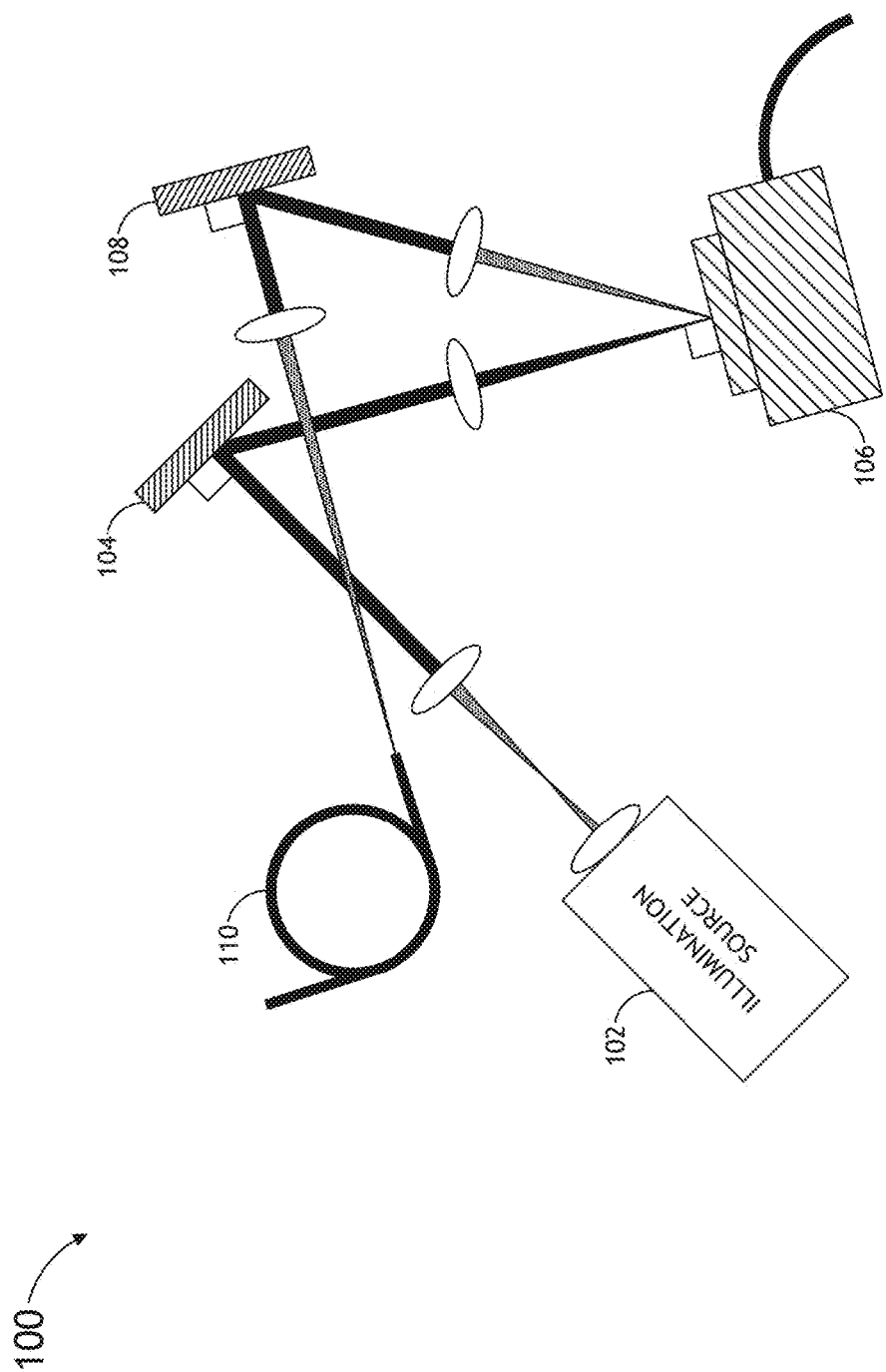

SPECTRAL CONTROL SYSTEM

PRIORITY

The present application claims priority to U.S. Non-Provisional application Ser. No. 13/945,352, entitled SPECTRAL CONTROL SYSTEM, By Amnon Manassen, Andrew V. Hill, Ohad Bachar, Avi Abramov, and Dania Negri, filed Jul. 18, 2013, which claims priority to U.S. Provisional Application Ser. No. 61/738,322, entitled SPECTRUM FLEXIBILITY OF OPTICAL METROLOGY, By Amnon Manassen et al., filed Dec. 17, 2012, and U.S. Provisional Application Ser. No. 61/808,555, entitled SPECTRUM FLEXIBILITY OF OPTICAL METROLOGY, By Amnon Manassen et al., filed Apr. 4, 2013. The foregoing non-provisional and provisional applications are hereby incorporated by reference in their entirety.

TECHNICAL FIELD

The present disclosure generally relates to the field of optical systems and more particularly to an optical system for controlling spectral attributes of illumination.

BACKGROUND

Modern process control targets are subject to process developments designed for smaller features. For instance, optical metrology targets are being fabricated with thinner layers and materials with different optical constants. Developments in target design and other factors increase measurement sensitivity to the spectral content of probing beams. Accordingly, spectrally controlled illumination is often employed to enable monitoring and control of the effect of wavelength on measurement.

In some imaging and angular scatterometry systems, spectral bands are selected using filters. However, a bandwidth of a few tens of nanometers is required in order to maintain adequate precision*MAM performance. Spectroscopic scatterometers often include spectrometers for detection of illumination spectra. Imaging and angular scatterometry suffer from a limited choice of spectral structures which limits measurement potential because of the limited number of wavelength structures available per target. Similar limitations apply for spectroscopic scatterometry, because of the limited number of angular structures available for selection. There is a need in the art for increased configurability in spectral control systems.

SUMMARY

In one aspect, the disclosure is directed to a spectral control system and associated method, where the spectral control system includes at least a dispersion path, a spectral controller, and a combination path. One or more dispersive elements disposed along a dispersion path are configured to receive at least a first portion of illumination directed along the dispersion path from at least one illumination source. The dispersive elements are further configured to disperse the first portion of the illumination into a first plurality of dispersed portions of illumination. At least one spectral controller is configured to receive the first plurality of dispersed portions of illumination from the dispersion path. The spectral controller is further configured to block an excluded selection of the first plurality of dispersed portions of illumination and direct a transmitted selection of the first plurality of dispersed portions of illumination along the combination path. One or more combination elements disposed along the combination path are configured to combine the transmitted selection of the first plurality of dispersed portions of illumination into substantially coaxial illumination directed along an illumination path.

In another aspect, the disclosure is directed to a spectral control system and associated method, where the spectral control system includes a plurality of spectral control paths and at least one optical switch. At least a first optical switch is configured to direct illumination emanating from at least one illumination source along a selected spectral control path. Each spectral control path may be configured according to selected spectral attributes. For instance, a first spectral control path may be configured to filter out a first selection of illumination spectra, and a second spectral control path may be configured to filter out a second (different) selection of illumination spectra. The optical switch may allow rapid spectral control by switching from one preconfigured spectral control path to another. The spectrally controlled illumination from the selected path is directed along an illumination path. In some embodiments, the system further includes a second optical switch working in parallel with the first optical switch to direct spectrally controlled illumination received from the selected spectral control path along the illumination path.

In another aspect, the disclosure is directed to an optical metrology system and associated method, where the optical metrology system includes a spectral control system, such as the spectral control system described in at least one of the preceding paragraphs or as further described below. The optical metrology system may further include at least one illumination source, an optical measurement head, at least one detector, and at least one computing system communicatively coupled to the detector. The illumination source is configured to provide illumination along an optical path to the spectral control system. The optical measurement head is configured to illuminate a sample disposed upon a sample stage utilizing at least a portion of (spectrally controlled) illumination received from the illumination path of the spectral control system. The detector is configured to receive illumination scattered, reflected, or radiated from the sample. The computing system is configured to determine at least one spatial attribute of the sample based upon the illumination scattered, reflected, or radiated from the sample.

The spectral control system may enable the optical measurement head to illuminate a first portion of the sample with a first portion of illumination including a first selection of illumination spectra, a second portion of the sample with a second portion of illumination including a second selection of illumination spectra, and so on. In some embodiments, different layers of a sample are thus analyzed using illumination with selected spectral attributes for enhanced measurement capability.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which:

FIG. 1A is a block diagram illustrating a system for controlling spectral attributes of illumination, in accordance with an embodiment of this disclosure;

DETAILED DESCRIPTION

Reference will now be made in detail to the subject matter disclosed, which is illustrated in the accompanying drawings.

FIGS. 1A through 7 generally illustrate a system and method for controlling spectral attributes of illumination to improve optical metrology results. According to various aspects of the disclosure, spectral structures may be selected or configured using a spectral control system to achieve specified levels of contrast, performance, and accuracy. As angular and spectral scatterometry are two faces of Bragg diffraction, it is advantageous to measure and control angle and spectrum for improved performance. Spectroscopic scatterometry results have shown that sensitivity can be achieved over a range of many tens of nanometers. Accordingly, a spectral structure including selected sensitive portions of the spectra will lead to improved results. Further, angular scatterometry measurements may be taken with a selected spectral structure without laser coherence effects on one side and limited precision*MAM penalty when using simple filters on the other side. In spectroscopic scatterometry, the ability to select a spectral structure may further enable replacement of a spectrometer with a simple detector by integrating the signal from a predefined spectrum.

Figure 1B:
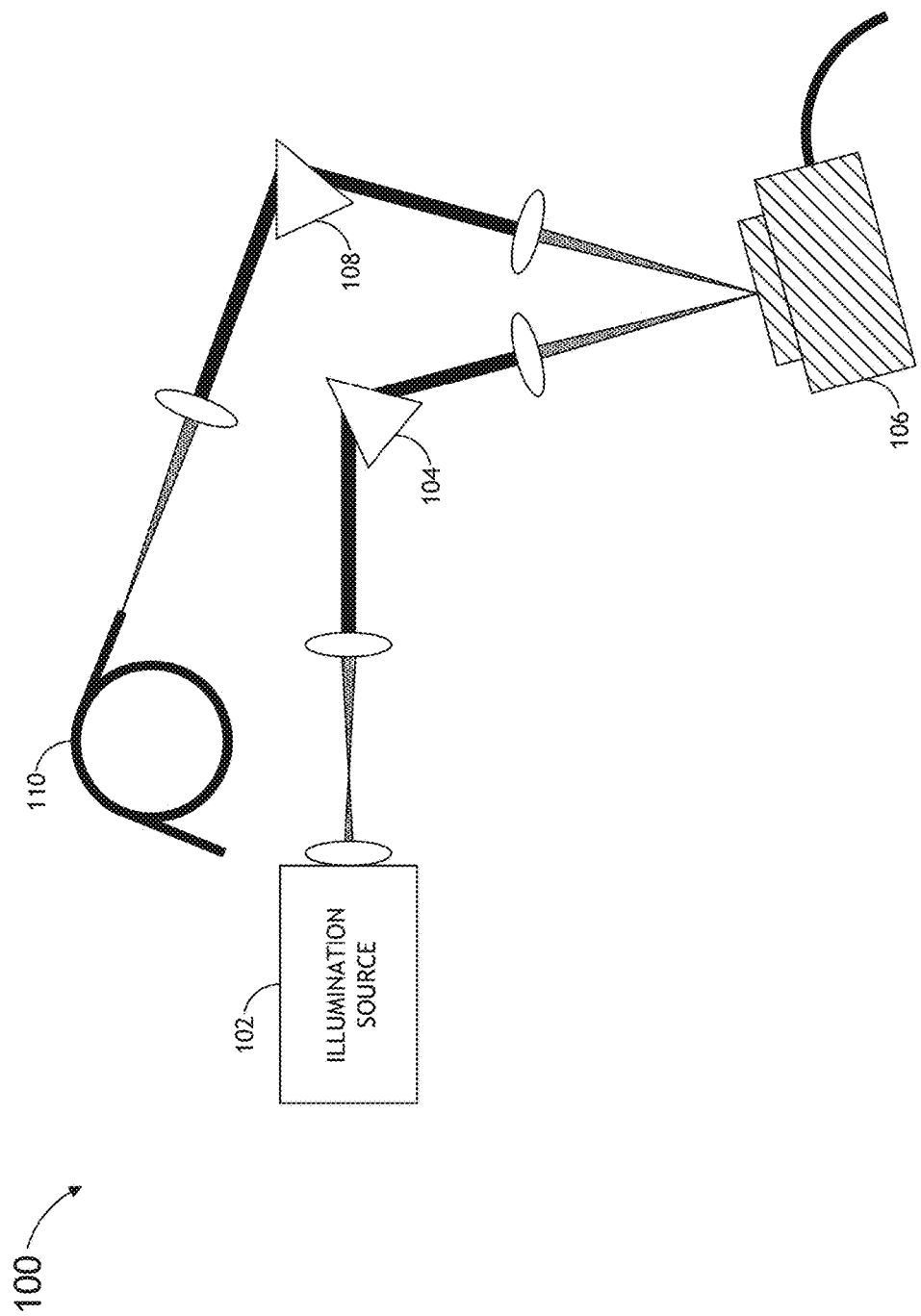
FIG. 1B is a block diagram illustrating the spectral control system, wherein dispersive elements of the system include optical prisms, in accordance with an embodiment of this disclosure.
Figure 1C:
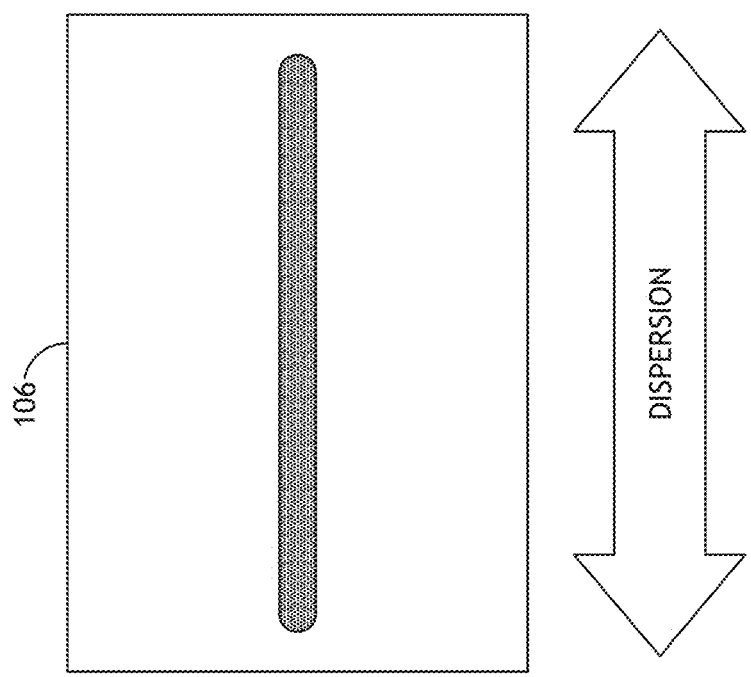
FIG. 1C is a view of illumination dispersed across a surface of a spectral controller of the spectral control system, in accordance with an embodiment of this disclosure.

FIGS. 1A through 1C illustrate embodiments of a spectral control system 100 including a dispersion path with one or more dispersive elements 104 and a combination path with one or more combination elements 108. The system 100 is configured to receive illumination directed along the dispersion path by at least one illumination source 102, such as a laser driven light source (LDLS), a laser sustained plasma (LSP), or any other broadband illuminator. The one or more dispersive elements 104 may include diffraction gratings or prisms (illustrated in FIG. 1B) configured to disperse at least a portion of the illumination directed along the dispersion path into a plurality of dispersed portions of illumination. For example, at least a first dispersive element 104 may be configured to disperse a first portion of illumination defined by a first spectral band or range.

The resulting dispersed portions of illumination may appear as a spectral continuum, as shown in FIG. 1C. The dispersed portions of illumination are directed from the dispersion path to at least one spectral controller 106, such as a mirror array (e.g. DLP micro-mirror array), a plurality of active shutters, a plurality of selectable filters or masks, or any other spatial light modulator (SLM) known to the art. The spectral controller 106 may be configured to block or stop a selection of the dispersed portions of illumination, thereby excluding the corresponding illumination spectra. The spectral controller 106 may be further configured to transmit or direct the remaining portions of dispersed illumination along the combination path. The one or more combination elements 108 may include a second set of diffraction gratings or prisms configured to recombine the transmitted selection of dispersed illumination into substantially coaxial (i.e. undispersed) illumination. The recombined spectrally controlled illumination may then be directed along an illumination path to an output source, such as an optical measurement head of an optical metrology system, such as an angular or spectroscopic scatterometry metrology system.

The various optical "paths" described herein may be delineated by a plurality of optical elements, such as one or more of: focusing lenses, coupling lenses, polarizers, beam splitters/combiners, optical fibers, dispersive elements, combination elements, and the like. For example, as illustrated in FIGS. 1A and 1B, the illumination path may include a coupling lens configured to direct the spectrally controlled illumination into an optical fiber 110 (e.g. A500 square-core fiber) for delivery to a selected output source. In some embodiments, for example, an optical measurement head of an optical metrology system may include the output end of the optical fiber 110 or may be configured to receive spectrally controlled illumination from the output end of the optical fiber 110.

According to various embodiments, the spectral controller 106 may include or may be driven by at least one computing system. Further, it should be recognized that the various steps and functions described throughout the present disclosure may be carried out by a single computing system or by multiple computing systems. For example, the one or more computing systems may include, but is not limited to, a personal computing system, mainframe computing system, workstation, image computer, parallel processor, or any other device known in the art. In general, the term "computing system" may refer to at least one single-core or multiple-core processor configured to execute program instructions from communicatively coupled carrier media.

Further, the spectral controller 106 may include one or more actuators driven by the computing system to configure an array of mirrors, open and close active shutters, rotate a filter wheel to select an appropriate spectral filter, or perform any other spectral programming/control activity. In some embodiments, the spectral controller 106 includes a DLP micro-mirror array (e.g. TEXAS INSTRUMENTS DLP5500) enabling configuration of spectral structures or selection of predetermined spectral structures by activating or deactivating specified array elements. The programmable nature of the spectral controller 106 enables access to an increased number of spectral structures defined by predetermined and/or customized configurations. For example, the spectral configurations may be loaded from storage media and/or determined according to user input or specified according to system, device, or sample parameters.

Figure 2A:
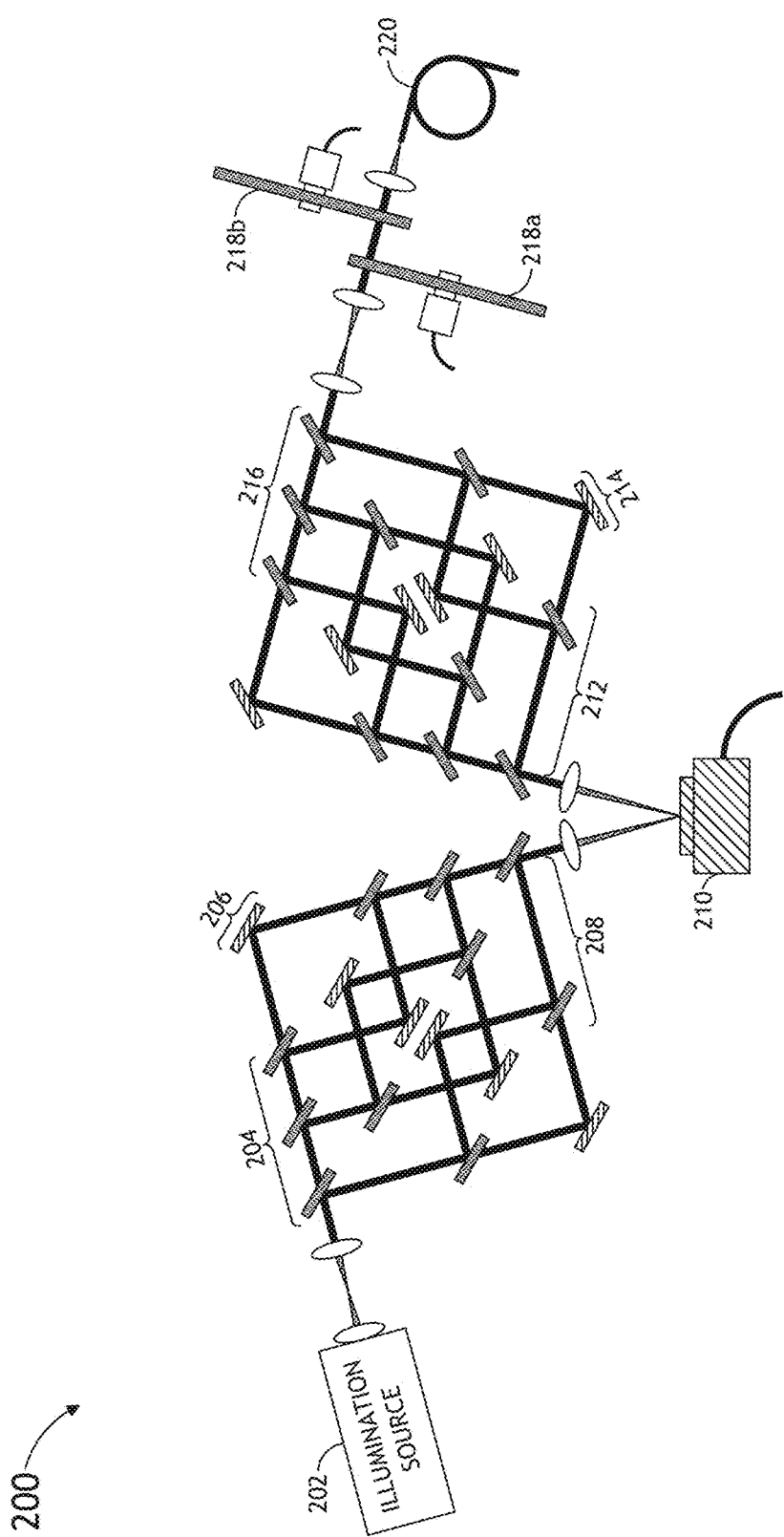
FIG. 2A is a block diagram illustrating a multi-path system for controlling spectral attributes of illumination, wherein the system includes a plurality of dichroic splitters and a plurality of dispersive elements for multi-path dispersion of selected spectral bands, in accordance with an embodiment of this disclosure.
Figure 2B:
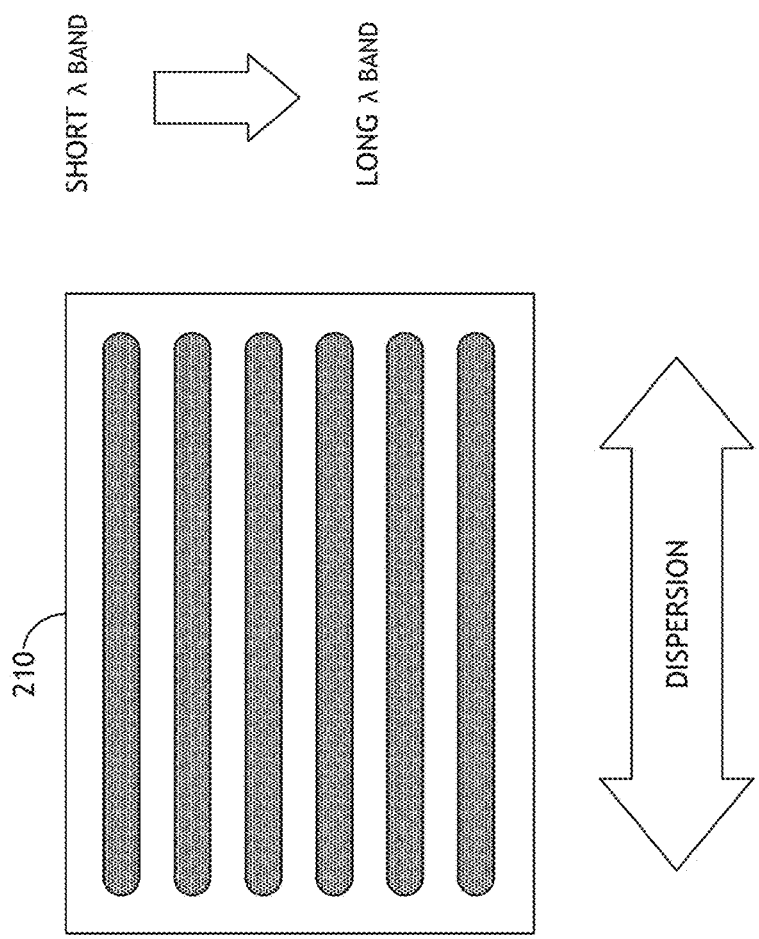
FIG. 2B is a view of illumination from the selected spectral bands dispersed across a surface of a spectral controller of the multi-path spectral control system, in accordance with an embodiment of this disclosure.

FIGS. 2A and 2B illustrate an embodiment of a spectral control system 200 including multiple sub-dispersion paths and sub-combination paths to enable wider spread of illumination spectra. Broadband illumination delivered along the dispersion path by an illumination source 202 may be split into a selected number of portions, each within a respective spectral band. Then each portion may be dispersed into a plurality of dispersed portions forming a plurality of spectral continuums (as shown in FIG. 2B) for higher resolution control of the illumination spectra. For example, illumination may be split among six sub-dispersion paths leading to six respective dispersive elements 206 for as much as six times the resolution attainable with a single-line dispersion path. The foregoing example is illustrative of the increased resolution of spectral control attainable with multi-path dispersion. It is noted, however, that the number of sub-paths is arbitrary and no limitation is intended by the illustrative examples provided herein.

In some embodiments, the dispersion path may include a first plurality of dichroic splitters 204 configured to receive illumination directed along the dispersion path from the illumination source 202. The dichroic splitters 204 may be further configured to direct portions illumination within specified spectral bands or ranges along sub-dispersion paths leading to the respective dispersive elements 206. For example, the dichroic splitters 204 may be configured to divide illumination received from the illumination source 202 into a plurality of bands within the range of 300 to 900 nm. The dispersion path may further include a second plurality of dichroic splitters 208 configured to direct the dispersed portions of illumination from each sub-dispersion path along a common path to at least one spectral controller 210.

FIG. 2B illustrates the dispersed portions of illumination from each sub-path directed onto a surface of the spectral controller 210. By dividing the illumination into a plurality of portions within respective spectral bands and then dispersing each portion into a spread out spectral continuum, the spectral controller 210 is enabled to exclude selected portions within each of the plurality of spectral bands. Since the illumination is spread over a greater surface (e.g. six times as much surface area) of the spectral controller 210, the spectral controller 210 is enabled to control the excluded/transmitted selection of illumination spectra with improved resolution due to the increase number of array elements that can be activated/deactivated to affect illumination spectra. Higher resolution without undue cost and system complexity may be achieved by separating illumination into multiple strips directed at a single spatial light modulator. Furthermore, recombining the spectrally controlled illumination along a common illumination path preserves spectral brightness of the illumination source 202.

As shown in FIG. 2A, the combination path may include a reversed configuration of elements that mirrors the dispersion path. For example, the combination path may include a first plurality of dichroic combiners 212 configured to direct transmitted portions of dispersed illumination from the spectral controller 210 along a plurality of sub-combination paths leading to respective combination elements 214. The combination path may further include a second plurality of dichroic combiners 216 configured to direct the substantially coaxial (undispersed) illumination received from each combination element 214 (i.e. each sub-combination path) onto a common illumination path. In some embodiments, the illumination path may further include one or more neutral density filters 218 configured to control an intensity level of the spectrally controlled illumination. As discussed above, the illumination path may be delineated by any number of optical elements, such as an optical fiber 220 configured to deliver at least a portion of spectrally controlled illumination to an optical measurement head or another output source.

It is noted that the terms "dichroic splitter" and "dichroic combiner" may be interchangeably utilized to reference an illumination splitting or combining functionality. However, the term "dichroic splitter" is generally used herein to refer to a dichroic splitter/combiner disposed along the dispersive path, and the term "dichroic combiner" is generally used herein to refer to a dichroic splitter/combiner disposed along the combination path. Accordingly, the use of either term should not be understood to limit the disclosure in any way.

Figure 3:
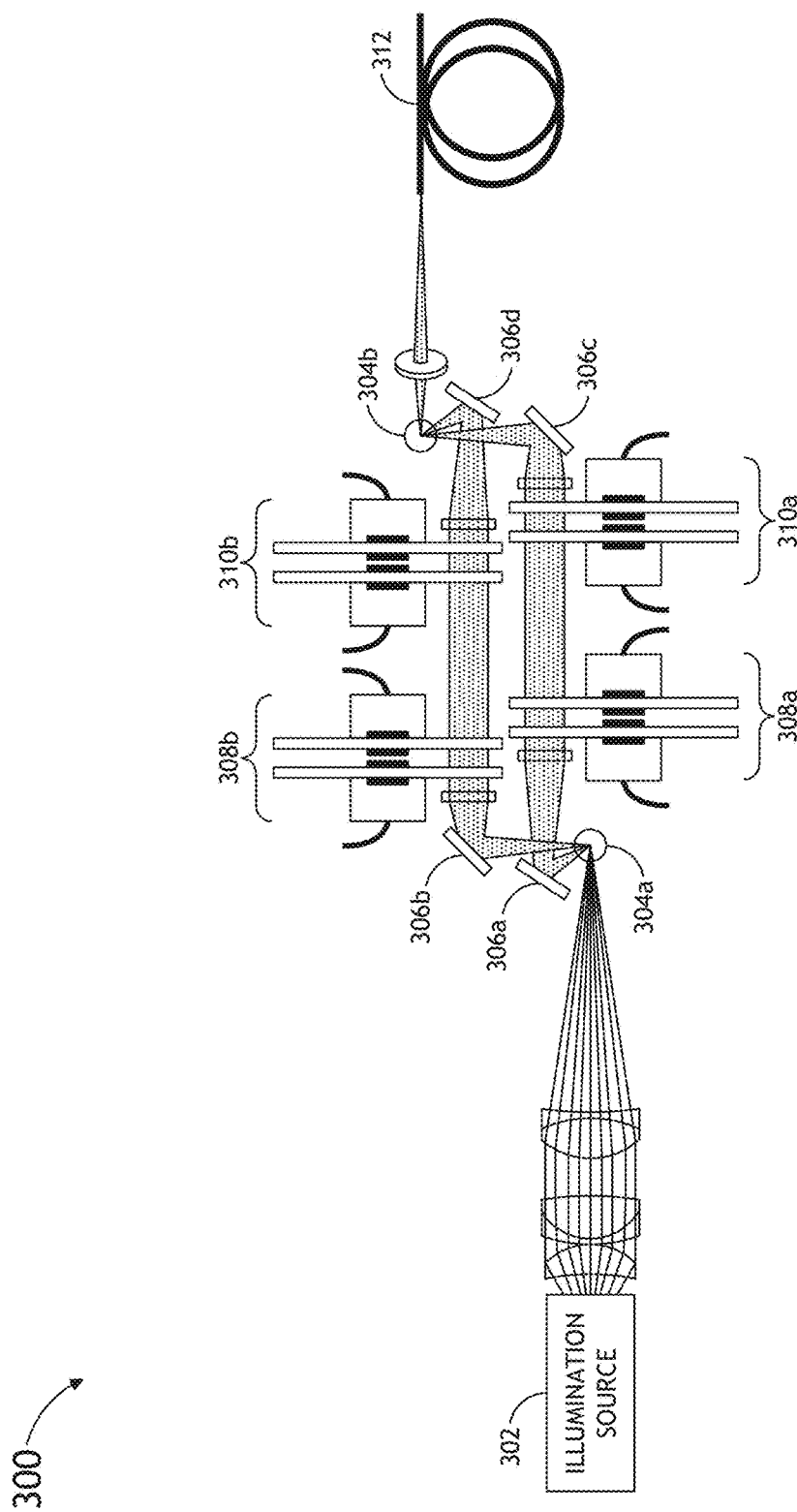
FIG. 3 is a block diagram illustrating a system for controlling spectral attributes of illumination, in accordance with an embodiment of this disclosure.

FIG. 3 illustrates an embodiment of a spectral control system 300 including multiple spectral control paths, where selection of a control path determines spectral attributes of output illumination. The system 300 may include at least one illumination source 302, such as sources 202 or 102 described above. The illumination source 302 may be configured to provide illumination along a switching path defined by one or more optical elements or free space to an optical switch 304A. In some embodiments, the optical switch 304A includes a switching mirror assembly, such as an actuator (e.g. motor or servo) coupled to a mirror, a galvanometer ("galvo") mirror, or galvo scanner. The optical switch 304A may be configured to direct at least a portion of illumination received from the illumination source 302 along a selected spectral control path. For example, a first spectral control path and a second spectral control path are illustrated following the optical switch 304A in FIG. 3. It is noted, however, that any number (i.e. two or more) of spectral control paths may be employed without substantial deviation from the architecture described herein.

In some embodiments, the system 300 includes fold mirrors 306A-306D or other optical elements defining the spectral control paths to reduce overall system footprint by allowing flexibility in disposition of one spectral control path relative to another. For example, the optical switch 304A may be configured to direct illumination along a selected one of a first spectral control path defined by fold mirrors 306A and 306C or a second spectral control path defined by fold mirrors 306B and 306D. In some embodiments, the system 300 further includes a second optical switch 304B working in parallel with the first optical switch 304A. The second optical switch 304B may be configured to receive spectrally controlled illumination from the selected spectral control path and further configured to direct the spectrally controlled illumination along an illumination path. Other optical switching arrangements may be employed without departing from the scope of this disclosure. For instance, a single optical switch 304 may be configured to direct illumination from the illumination source 302 along a selected spectral control path, where the output spectrally controlled illumination is directed along the illumination path by an arrangement of optical elements known to the art, such as any combination of prisms, lenses, optical fibers, or the like.

Each spectral control path may include at least one spectral controller 308 configured to block a portion of illumination including an excluded selection of illumination spectra. Each spectral controller 308 may be further configured to direct a portion of illumination including a transmitted selection of illumination spectra along the illumination path, either directly or via optical elements defining a remainder of the respective spectral control path. The spectral controllers 308 may include a plurality of selectable filters. For example, each spectral controller 308 may include a color wheel or another actuatable structure supporting a plurality of predefined filters, where a filter is selected or deselected by actuation within or out of the respective spectral control path. Alternatively, each spectral controller 308 may include one of a plurality of filters selected by manual disposition within a receiving slot.

The optical switch 304 may enable rapid switching between a plurality of preconfigured spectral control paths, such as a first path configured according to a first spectral controller 308A and a second path configured according to a second spectral controller 308B. Further, when one spectral control path is selected, the other spectral control path or paths may be reconfigured. For example, the second spectral controller 308B may be reconfigured while the first spectral controller 308A is active. In some embodiments, for added flexibility of spectral control and increased switching capability, each spectral controller 308 may include a highly configurable sub-spectral control system, such as system 100 or system 200 described above.

The system 300 may further include one or more neutral density filters 310 configured to control intensity of the output spectrally controlled illumination. A neutral density filter 310 may be disposed along the illumination path or respective neutral density filters 310A and 310B may be disposed in each spectral control path. In some embodiments, the system 300 further includes one or more optical elements defining the illumination path, such as an optical fiber 312 (e.g. multi-mode optical fiber) which may be fed by a coupling lens.

With regards to system 300 as well as systems 100 and 200, the output spectrally controlled illumination may be fed into an optical measurement head for an optical metrology, inspection, or analysis system. In some embodiments, the optical measurement head may further include or may be integrated with an output end of the optical fiber 312 (also applicable to optical fibers 110 or 220) transferring at least a portion of the output spectrally controlled illumination.

Figure 4:
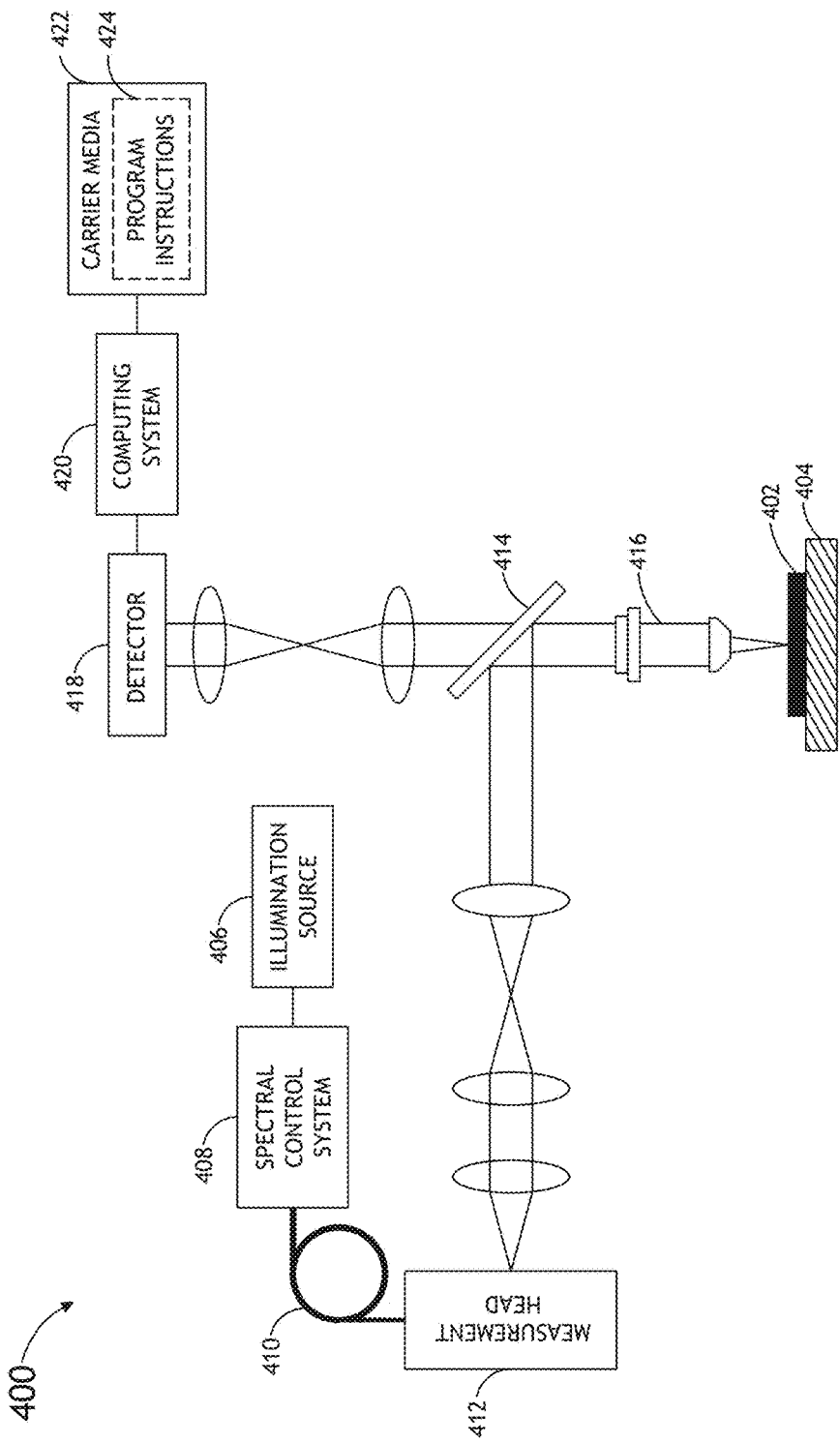
FIG. 4 is a block diagram illustrating an optical metrology system including a spectral control system, in accordance with an embodiment of this disclosure.

FIG. 4 illustrates an optical metrology system 400, such as an angular or spectroscopic scatterometry system, configured to determine defect characteristics or spatial attributes of at least one sample 402, such as a semiconductor wafer or mask. Optical metrology systems are well known in the art. The following description is illustrative of an embodiment; however, those skilled in the art will appreciate that concepts described herein may be extended to alternative embodiments of optical metrology or inspection systems without departing from the scope of this disclosure.

In an embodiment, the system 400 may include a stage 404 configured to support a sample 402. The stage 404 may include or may be coupled to at least one actuator configured to translate or rotate the stage 404. Accordingly, the stage 404 may be configured to support the sample 402 at a selected position for receiving illumination delivered along an illumination path to a selected region of the sample surface. In some embodiments, the system 400 is further configured for scanning illumination along a surface of the sample 402.

The system 400 may include at least one illumination source 406 feeding into a spectral control system 408, such as system 100, system 200, or system 300 described above. The spectral control system 408 may be configured to deliver illumination via free space coupling or fiber coupling via an optical fiber 410 to an optical measurement head 412 of the system 400. As discussed above with regard to some embodiments, the optical measurement head 412 may further include or may be integrated with the output end of the optical fiber 410. The optical measurement head 412 may be configured to provide at least a portion of the spectrally controlled illumination along the illumination path to illuminate a surface of the sample 402.

In some embodiments, the optical measurement head 412, in accordance with the spectral control system 408, is configured to illuminate different portions (e.g. semiconductor device layers) of the sample 402 with portions of illumination having different spectral attributes. For example, the optical measurement head 412 may be configured to illuminate a first portion (e.g. process layer) of the sample 402 with illumination including a first selection of spectra and a second portion (e.g. resist layer) of the sample 402 with illumination including a second selection of spectra. The transmitted selection of illumination spectra utilized to illuminate the sample 402 or different layers of the sample 402 may be selected according to various sample, layer, and/or measurement characteristics. For example, the transmitted selection of illumination spectra may be selected and controlled according to overlay sensitivity or a predetermined or predicted level of accuracy. In some embodiments, different measurement recipes are tested over time. As such, the transmitted selection of illumination spectra may be based upon at least one preceding measurement.

Illumination optics including, but not limited to, a beam splitter 414 and an objective lens 416 may be disposed along the illumination path. For example, the beam splitter 414 may be configured to direct at least a portion of the illumination through the objective lens 416 to the sample surface. Illumination scattered, reflected, or radiated by the sample 402 is directed along a collection path delineated by collection optics to at least one detector 418, such as a spectrometer, camera, or any other photodetector. The system 400 may further include a computing system 420 communicatively coupled to the detector 418. The computing system 420 may be configured to determine at least one spatial attribute of the sample 402 or defect information based upon the detected illumination in accordance with a metrology or detection algorithm embedded in program instructions 424 executed from at least one carrier medium 422. In some embodiments, the computing system 420 is further configured to drive the spectral control system 408. For example, the computing system 420 may be configured to drive components of the spectral control system 408, such as a spectral controller, optical switch, or the like.

In some embodiments, the system 400 is configured for spectroscopic scatterometry where the detector 418 includes a simple detector configured for integrating the signal received according to a predetermined controlled illumination spectrum. In some embodiments, the system 400 is configured for combined angular and spectroscopic scatterometry where the detectors 418 include a set of fiber spectrometers with inputs mounted to a pupil of the system 400 for analyzing spectrum and its dependence on pupil position. In some embodiments, the system 400 is configured for combined angular and spectroscopic scatterometry where a plurality of fiber coupled detectors 418 with inputs mounted to the pupil are configured scan over the predetermined controlled spectral range. The foregoing embodiments are illustrative of measurement improvement and increased system capability resulting from the enhanced spectral control described herein.

Figure 5:
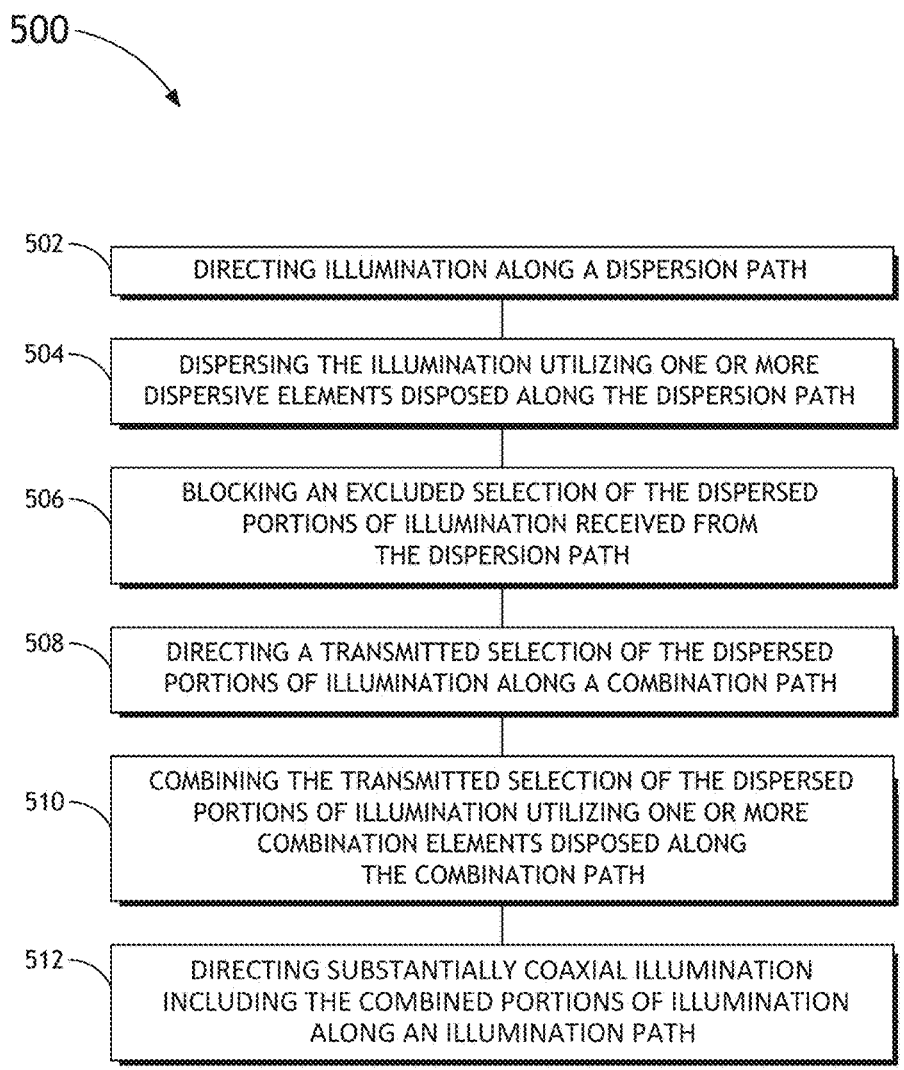
FIG. 5 is a flow diagram illustrating a method of controlling spectral attributes of illumination, in accordance with an embodiment of this disclosure.

FIG. 5 illustrates a method 500 of controlling spectral attributes of illumination in accordance with system 100 and/or system 200. As such, method 500 includes steps for executing any of the above described functions or implementing any of the above described features in addition to the steps that follow. It is noted, however, that one or more steps of method 500 may be executed via systems or configuration beyond the embodiments of systems 100 and 200 described above. Method 500 should be construed to encompass any system or device configured to carry out the following steps.

At steps 502 and 504, illumination directed along a dispersion path is dispersed by one or more dispersion elements and further directed to a spectral controller. In some embodiments, the dispersion path includes a first plurality of splitters/combiners configured divide the illumination among a selection of spectral ranges, each portion being directed along a sub-dispersion path to a respective dispersion element. The dispersion path may further include a second plurality of splitters/combiners configured to receive dispersed portions of illumination from the plurality of dispersion elements. The dispersed portions of illumination may be directed from the second plurality of splitters/combiners to the spectral controller such that each selection of the dispersed portions is delivered forming a spectral continuum across the surface of the spectral controller, as illustrated in FIG. 1C (single-path) and FIG. 2B (multi-path).

At steps 506 and 508, the illumination spectrum controlled by blocking selected portions of the dispersed illumination from being transmitted along a combination path. In some embodiments, the spectral controller excludes selected portions by activating/deactivating array elements or opening/closing active shutters. Accordingly, only selected portions of the spectrally dispersed illumination, hence only a selected portion of the illumination spectra, are transmitted along the combination path.

At step 510, the transmitted portions of dispersed illumination are recombined into substantially coaxial or undispersed illumination utilizing one or more combination elements. In some embodiments, for example, the combination elements may be similar to the dispersive elements in structure but arranged for functionally reversing the operation of the dispersive elements on the transmitted portions of illumination. At step 512, the undispersed (spectrally controlled) illumination is directed along an illumination path. For example, the spectrally controlled illumination may be directed through a coupling lens feeding at least a portion of the illumination into an optical fiber coupled to an optical measurement head.

Figure 6:
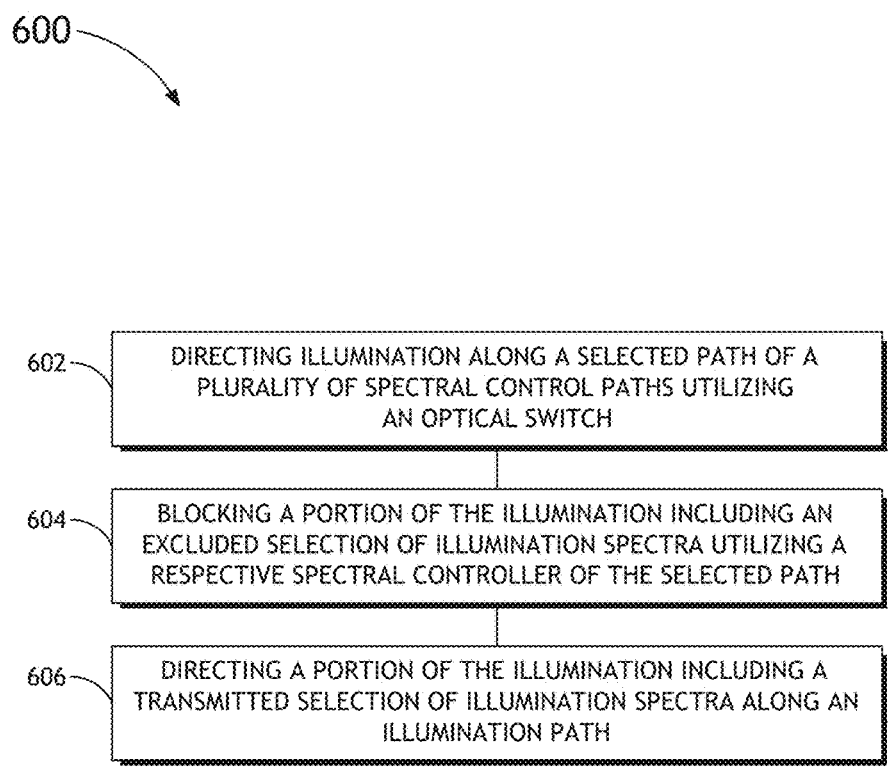
FIG. 6 is a flow diagram illustrating a method of controlling spectral attributes of illumination, in accordance with an embodiment of this disclosure.

FIG. 6 illustrates a method 600 of controlling spectral attributes of illumination in accordance with system 300. As such, method 600 includes steps for executing any of the above described functions or implementing any of the above described features in addition to the steps that follow. It is noted, however, that one or more steps of method 600 may be executed via systems or configuration beyond the embodiments of system 300 described above. Method 600 should be construed to encompass any system or device configured to carry out the following steps.

At step 602, at least a portion of illumination emanating from an illumination source 302 is directed along a selected path of a plurality of spectral control paths via at least one optical switch 304. In some embodiments, a first optical switch 304A operates in parallel with a second optical switch 304B. For example, the first optical switch 304A may direct illumination along the selected spectral control path, and the second optical switch 304B may direct spectrally controlled illumination received from the selected spectral control path along an illumination path.

At step 604, a spectral controller 308 disposed within the selected spectral control path blocks a first portion of illumination including an excluded selection of illumination spectra. At step 606, the second portion of illumination including a transmitted selection of illumination spectra is directed from the spectral controller 308 along the illumination path, either directly or indirectly (e.g. via the second optical switch 304B). Further, an intensity level of the spectrally controlled illumination may be adjusted via one or more neutral density filters disposed within each spectral control path or disposed within the illumination path. In some embodiments, the spectrally controlled illumination is further directed along an optical fiber feeding into an optical measurement head or another output source, as discussed above.

Figure 7:
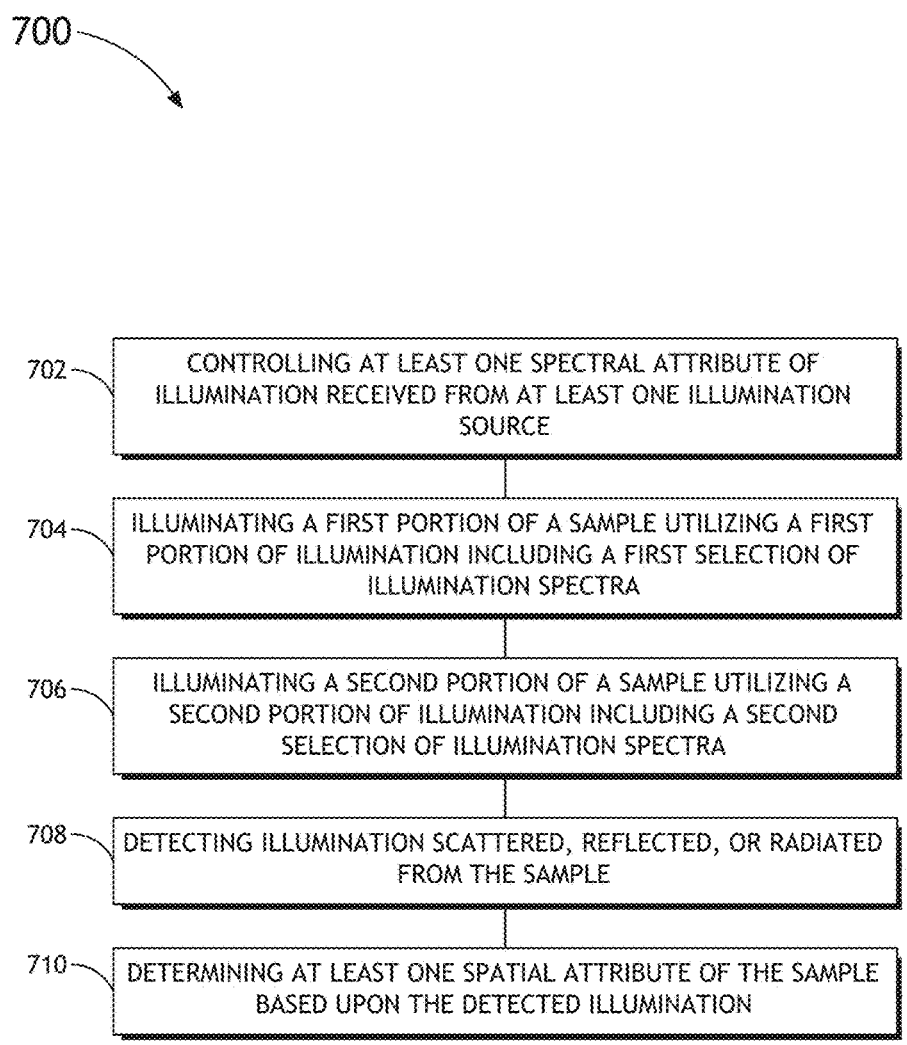
FIG. 7 is a flow diagram illustrating a method of performing optical metrology, in accordance with an embodiment of this disclosure.

FIG. 7 illustrates a method 700 of performing optical metrology utilizing spectrally controlled illumination in accordance with system 400. As such, method 700 includes steps for executing any of the above described functions or implementing any of the above described features in addition to the steps that follow. It is noted, however, that one or more steps of method 700 may be executed via systems or configuration beyond the embodiments of system 400 described above. Method 700 should be construed to encompass any system or device configured to carry out the following steps.

At step 702, at least one spectral attribute of illumination emanating from an illumination source 406 is controlled via a spectral control system 408. For example, the spectral control system 408 may execute the steps of method 500 or method 600 to provide spectrally controlled illumination including a transmitted selection of illumination spectra along an illumination path (e.g. via optical fiber 410) to an optical measurement head 412. In some embodiments, the transmitted selection of illumination spectra (i.e. the spectral attributes of the illumination) are selected according to overlay sensitivity, measurement accuracy, and/or various sample characteristics. In some embodiments, the selected spectral attributes are based upon one or more preceding measurements. For example, different measurement recipes may be tested over time to select an optimal or near optimal spectral configuration.

Various portions of a metrology sample 402, such as a semiconductor wafer, mask, or patterned target structure, may respond differently to illumination spectra. For example, a first portion (e.g. process layer) and a second portion (e.g. resist layer) may be more or less sensitive to certain portions of an illumination spectrum. It may be advantageous to analyze each portion of the sample 402 utilizing a different spectral configuration. As such, some embodiments may include steps 704 and 706 of illuminating a first portion of the sample 402 utilizing illumination including a first selection of illumination spectra and a second portion of the sample 402 utilizing illumination including a second selection of illumination spectra.

At step 708 and 710, illumination scattered, reflected, or radiated from the sample 402 is detected, and at least one spatial attribute of the sample 402 is determined utilizing information (e.g. intensity, waveform, polarity, spectral content, image content) associated with the detected illumination. In some embodiments, steps 708 and 710 are repeated for each portion (e.g. device layer) of the sample 402 analyzed utilizing different illumination spectra. Accordingly, different samples 402 or different portions of the same sample 402 can be analyzed with improved sensitivity by illuminating each sample 402 or sample portion with illumination including individually selected illumination spectra.

Those having skill in the art will further appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for controlling at least one spectral attribute of illumination, comprising:
   a plurality of dispersive elements;
   at least one spectral controller;
   a first plurality of dichroic splitters configured to direct portions of illumination from the at least one illumination source along respective paths to the plurality of dispersive elements;
   a second plurality of dichroic splitters configured to direct dispersed portions of illumination from the plurality of dispersive elements to the least one spectral controller, wherein the spectral controller is configured to block an excluded selection of the dispersed portions of illumination, and further configured to direct a transmitted selection of the dispersed portions of illumination along a combination path; and
   one or more combination elements disposed along the combination path, the one or more combination elements configured to combine the transmitted selection of the dispersed portions of illumination into substantially coaxial illumination directed along an illumination path.

2. The system of claim 1, wherein one or more of the plurality of dispersive elements include one or more diffraction gratings.

3. The system of claim 1, wherein the one or more combination elements include one or more diffraction gratings.

4. The system of claim 1, wherein one or more of the plurality of dispersive elements include one or more prisms.

5. The system of claim 1, wherein the one or more combination elements include one or more prisms.

6. The system of claim 1, wherein the at least one spectral controller includes a micro-mirror array.

7. The system of claim 1, wherein the at least one spectral controller includes a plurality of active shutters.

8. The system of claim 1, wherein the at least one spectral controller includes a plurality of selectable filters.

9. The system of claim 1, further comprising:
   a first plurality of dichroic combiners configured to direct portions of illumination from the at least one spectral controller along respective paths to the one or more combination elements; and
   a second plurality of dichroic combiners configured to direct combined portions of illumination from the one or more combination elements along the illumination path.

10. The system of claim 1, further comprising:
    one or more neutral density filters configured to control an intensity level of the substantially coaxial illumination directed along the illumination path.

11. The system of claim 1, wherein the illumination path includes at least one optical fiber configured to direct the substantially coaxial illumination to an optical measurement head of an optical metrology system.

12. An optical metrology system, comprising:
    at least one illumination source;
    a spectral control system configured to receive illumination emanating from the at least one illumination source and further configured to block a portion of illumination including an excluded selection of illumination spectra, and further configured to direct a portion of illumination including a transmitted selection of illumination spectra along an illumination path, wherein the spectral control system includes:
       a plurality of dispersive elements;
       at least one spectral controller;
       a first plurality of dichroic splitters configured to receive illumination emanating from the at least one illumination source, and further configured to direct multiple portions of the illumination along a plurality of dispersion paths to the plurality of dispersive elements;
       a second plurality of dichroic splitters configured to direct dispersed portions of illumination from the plurality of dispersive elements to the least at least one spectral controller, the at least one spectral controller configured to block an excluded selection of the dispersed portions of illumination;
    an optical measurement head configured to illuminate a sample disposed upon a sample stage utilizing at least a portion of illumination received from the illumination path, the optical measurement head being configured to illuminate at least a first portion of the sample utilizing a first portion of illumination including a first selection of illumination spectra and a second portion of the sample utilizing a second portion of illumination including a second selection of illumination spectra;
    at least one detector configured to receive illumination scattered, reflected, or radiated from the sample; and
    at least one computing system communicatively coupled to the at least one detector, the at least one computing system configured to determine at least one spatial attribute of the sample based upon the illumination scattered, reflected, or radiated from the sample.

13. The system of claim 12, wherein the first portion of the sample includes a process layer, and wherein the second portion of the sample includes a resist layer.

14. The system of claim 12, wherein the transmitted selection of illumination spectra is based upon at least one of overlay sensitivity and measurement accuracy.

15. The system of claim 12, wherein the transmitted selection of illumination spectra is based upon at least one preceding measurement.

16. The system of claim 12, wherein the spectral control system further includes:
a first plurality of dichroic combiners configured to receive a transmitted selection of the dispersed portions of illumination from the at least one spectral controller, and further configured to direct the transmitted selection of the dispersed portions of illumination along a plurality of combination paths;
a plurality of combination elements, each combination element located along a respective one of the plurality of combination paths; and
a second plurality of dichroic combiners configured to direct combined portions of illumination from the plurality of combination elements along the illumination path.

17. The system of claim 12, further comprising:
one or more neutral density filters configured to control an intensity level of at least a portion of illumination directed along the illumination path.

18. The system of claim 12, wherein the illumination path includes at least one optical fiber configured to direct at least a portion of illumination to the optical measurement head.

19. A method of performing optical metrology, comprising:
controlling at least one spectral attribute of illumination received from at least one illumination source including blocking a portion of the illumination including an excluded selection of illumination spectra and directing a portion of the illumination including a transmitted selection of illumination spectra along an illumination path, wherein controlling the at least one spectral attribute of illumination received from the at least one illumination source includes:
directing portions of illumination from the at least one illumination source along respective paths to a plurality of dispersive elements utilizing a first plurality of dichroic splitters;
directing dispersed portions of illumination from the plurality of dispersive elements to at least one spectral controller utilizing a second plurality of dichroic splitters;
illuminating at least a first portion of a sample utilizing a first portion of illumination including a first selection of illumination spectra and a second portion of the sample utilizing a second portion of illumination including a second selection of illumination spectra;
detecting illumination scattered, reflected, or radiated from the sample; and
determining at least one spatial attribute of the sample based upon the illumination scattered, reflected, or radiated from the sample.

20. The method of claim 19, wherein controlling the at least one spectral attribute of the illumination received from the at least one illumination source includes:
selecting the transmitted selection of illumination spectra based upon at least one of overlay sensitivity and measurement accuracy.

21. The method of claim 19, wherein controlling the at least one spectral attribute of the illumination received from the at least one illumination source includes:
selecting the transmitted selection of illumination spectra based upon at least one preceding measurement.

22. The method of claim 19, wherein controlling the at least one spectral attribute of the illumination received from the at least one illumination source further includes:
blocking an excluded selection of the first plurality of dispersed portions of illumination utilizing at least one spectral controller;
directing a transmitted selection of the first plurality of dispersed portions of illumination from the at least one spectral controller along a combination path;
combining the transmitted selection of the first plurality of dispersed portions of illumination utilizing one or more combination elements; and
directing substantially coaxial illumination including the combined portions of illumination along an illumination path.

23. The method of claim 22, wherein controlling the at least one spectral attribute of the illumination received from the at least one illumination source further includes:
directing selected portions of illumination from the at least one spectral controller along respective paths to a plurality of combination elements utilizing a first plurality of dichroic combiners; and
directing combined portions of illumination from the plurality of combination elements along the illumination path utilizing a second plurality of dichroic combiners.

24. A method of performing optical metrology comprising:
controlling at least one spectral attribute of illumination received from at least one illumination source including blocking a portion of the illumination including an excluded selection of illumination spectra and directing a portion of the illumination including a transmitted selection of illumination spectra along an illumination path, wherein controlling the at least one spectral attribute of illumination received from the at least one illumination source includes:
directing illumination received from the at least one illumination source along a selected path of a plurality of spectral control paths utilizing an optical switch, each spectral control path of the plurality of spectral control paths including at least one spectral controller;
blocking the portion of the illumination including the excluded selection of illumination spectra utilizing a respective spectral controller of the selected path of the plurality of spectral control paths; and
directing the portion of the illumination including the transmitted selection of illumination spectra along the illumination path;
illuminating at least a first portion of a sample utilizing a first portion of illumination including a first selection of illumination spectra and a second portion of the sample utilizing a second portion of illumination including a second selection of illumination spectra;
detecting illumination scattered, reflected, or radiated from the sample; and determining at least one spatial attribute of the sample based upon the illumination scattered, reflected, or radiated from the sample.

25. The method of claim 24, wherein directing the portion of the illumination including the transmitted selection of illumination spectra along the illumination path includes:
directing illumination received from the selected path of the plurality of spectral control paths along the illumination path utilizing a second optical switch.

26. The method of claim 19, further comprising:
controlling an intensity level of the substantially coaxial illumination directed along the illumination path utilizing one or more neutral density filters.

27. The method of claim 19, further comprising:
directing the substantially coaxial illumination to an optical measurement head of an optical metrology system utilizing an optical fiber.

28. An optical metrology system, comprising:
at least one illumination source;
a spectral control system configured to receive illumination emanating from the at least one illumination source and further configured to block a portion of illumination including an excluded selection of illumination spectra, and further configured to direct a portion of illumination including a transmitted selection of illumination spectra along an illumination path, wherein the spectral control system includes:
a first optical switch configured to receive illumination emanating from the at least one illumination source, and further configured to direct the illumination along a selected path of a plurality of spectral control paths;
a plurality of spectral controllers, at least one spectral controller of the plurality of spectral controllers being disposed along each of the plurality of spectral control paths, the at least one spectral controller being configured to block a portion of the illumination including an excluded selection of illumination spectra; and
a second optical switch configured to receive a portion of the illumination including a transmitted selection of illumination spectra from the at least one spectral controller of the selected path of the plurality of spectral control paths, and further configured to direct the portion of the illumination including the transmitted selection of illumination spectra along the illumination path;
an optical measurement head configured to illuminate a sample disposed upon a sample stage utilizing at least a portion of illumination received from the illumination path, the optical measurement head being configured to illuminate at least a first portion of the sample utilizing a first portion of illumination including a first selection of illumination spectra and a second portion of the sample utilizing a second portion of illumination including a second selection of illumination spectra; and
at least one detector configured to receive illumination scattered, reflected, or radiated from the sample.

* * * * *